United States Patent
Sasai (10) Patent No.: US 7,639,860 B2
(45) Date of Patent: Dec. 29, 2009

(54) SUBSTRATE INSPECTION DEVICE

(75) Inventor: Masatoshi Sasai, Kyoto (JP)

(73) Assignee: Mega Trade Corp., Kyoto (JP)

( * ) Notice: Subject to any disclaimer, the term of this patent is extended or adjusted under 35 U.S.C. 154(b) by 616 days.

(21) Appl. No.: 10/583,660

(22) PCT Filed: Dec. 17, 2004

(86) PCT No.: PCT/JP2004/018947

§ 371 (c)(1),
(2), (4) Date: Jun. 21, 2006

(87) PCT Pub. No.: WO2005/062028

PCT Pub. Date: Jul. 7, 2005

(65) Prior Publication Data

US 2007/0147676 A1    Jun. 28, 2007

(30) Foreign Application Priority Data

Dec. 22, 2003  (JP) .................... 2003-425497

(51) Int. Cl.
G06K 9/00 (2006.01)
(52) U.S. Cl. .................... 382/141; 382/149; 382/151
(58) Field of Classification Search ............ 382/144, 382/145, 147, 149, 151, 205, 218, 209, 282, 382/283, 141; 348/125, 126, 128, 129, 130; 356/237.1, 237.2, 243.1, 243.4, 390, 394, 356/398, 71; 250/491.1, 492.2, 310, 307; 714/720, 766, E11.036, 805; 430/322, 5; 365/200, 201
See application file for complete search history.

(56) References Cited

U.S. PATENT DOCUMENTS

| 4,783,826 | A  | * | 11/1988 | Koso ....................... 382/147 |
| 5,555,316 | A  | * | 9/1996  | Tsujikawa et al. .......... 382/150 |
| 5,608,816 | A  | * | 3/1997  | Kawahara et al. .......... 382/149 |
| 6,327,379 | B2 | * | 12/2001 | Matsuyama et al. ........ 382/144 |
| 6,330,354 | B1 | * | 12/2001 | Companion et al. ........ 382/150 |
| 6,870,169 | B2 | * | 3/2005  | Obara et al. ............ 250/492.2 |
| 7,058,221 | B1 | * | 6/2006  | Shikata ................... 382/169 |

FOREIGN PATENT DOCUMENTS

| JP | 63-196980 A | 8/1988 |
| JP | 5-60535 A   | 3/1993 |

(Continued)

*Primary Examiner*—Sheela C Chawan
(74) *Attorney, Agent, or Firm*—Westerman, Hattori, Daniels & Adrian, LLP (57) ABSTRACT

In the substrate inspection apparatus 2 for inspecting a formation state of the pattern area 20 formed on the printed circuit board 1, since the inside area data generation means 7 for generating inspection data of the inside area 21b of the pattern area 20 to be inspected, the outside area data generation means 10 for generating inspection data in the ring-shaped area 22b of the outside, and the inside/outside determination means 9 and 11 for determining whether the pattern area is defective or not defective by comparing the generated inside area data and the outside area data with the predetermined reference data are provided, by applying a relaxed inspection reference to the inside of the pattern area 20 where a relatively large defect is allowed and applying a strict inspection reference to the outside of the pattern area 20 where even a fine defect is not allowed, it is possible to adequately detect a defect.

6 Claims, 7 Drawing Sheets

FOREIGN PATENT DOCUMENTS

| | | |
|---|---|---|
| JP | 6-58729 A | 3/1994 |
| JP | 11-014324 A | 1/1999 |
| JP | 11-337498 A | 12/1999 |
| JP | 2000-241130 A | 9/2000 |
| JP | 2003-86919 A | 3/2003 |

* cited by examiner

SUBSTRATE INSPECTION DEVICE

TECHNICAL FIELD

The present invention relates to a substrate inspection apparatus for inspecting a formation state of a pad, wiring pattern etc. formed on a printed circuit board.

BACKGROUND ART

In general, on a surface of a printed circuit board, pads, wiring patterns, resists, silkscreen printings etc. are provided and by being attached on a substrate inspection apparatus, the pads, wiring patterns etc. are inspected. As such substrate inspection apparatuses for inspecting pads or wiring patterns on a printed circuit board, various substrate inspection apparatuses have been proposed. For example, apparatuses described in the patent literature 1 or 2 shown below exist.

A substrate inspection apparatus described in the patent literature 1 includes an area discrimination part for discriminating pattern areas on a printed circuit board with respect to a taken image of a printed board and an inspection part having an inspection treatment part for performing a detecting processing of a defect to each pattern area on the printed circuit board. After area information is formed on the basis of colors different at every pattern regions in an area dividing part, an inspection processing part detects a defect at every pattern area by applying different design rules at every pattern area or comparing with a normal reference image. By the configuration, to a pattern area where even a fine defect is not allowed, a strict reference is applied and to a pattern area where a relatively large defect is allowed, a relaxed reference is applied to effectively detect defectives.

In a wiring pattern detection method described in the patent literature 2, a fatal region pattern which shows necessary indispensable regions corresponding to the center of a wiring pattern is compared with an inspected pattern obtained from wiring patterns on an object under test and a defect is detected from the non-coincidence of both patterns. In particular, in the patent literature 2, as shown in FIG. 14 in the patent literature 2, if a crack which intrudes a fatal region pattern P2 exists, it is determined to be defective, on the other hand, if a small crack which does not intrude the fatal region pattern P2 exists, it is determined to be non-defective.

Patent Literature 1: Japanese Unexamined Patent Application Publication No. 11-337498

Patent Literature 2: Japanese Unexamined Patent Application Publication No. 2000-241130

DISCLOSURE OF INVENTION

Problem to be Solved by the Invention

To the pads or wiring patterns formed on the printed circuit board (hereinafter, referred to as "pattern area"), scratches or unevenness are easily formed on the surfaces during the forming processing of the printed circuit board, and cracks or protruding parts are also easily formed to the outline part. With respect to the cracks or the protruding parts formed to the outline part, it is necessary to be strictly inspected because there is a possibility that a short circuit occurs with adjacent pads or wiring patterns. On the other hand, with respect to the surface of the pad, it is sometimes preferred to qualify the pad as non-defective if there is no quality failure even if a certain level of scratch exists. However, in conventional printed circuit board inspection methods, the pattern area is inspected as a whole and it has not been possible to precisely inspect the inside part and the outside part of the pattern area respectively.

Further, the inspection method in the patent literature 2 detects whether cracks which intrude the fatal region pattern exist or not and does not independently detect the outside area of the wiring pattern. Accordingly, in the inspection method in the patent literature 2, even in the case that a protrusion etc. which can cause a short circuit in the outside area of the pad or wiring pattern exists, it is not determined as defective because the fatal region pattern is not intruded by the protrusion.

The present invention has been made in view of the above-mentioned problems, and an object of the present invention is to provide a substrate inspection apparatus capable of more precisely and effectively inspect a pattern area formed on a surface of a substrate.

Means for Solving the Problem

To solve the above problems, in the present invention, a substrate inspection apparatus for inspecting a formation state of a pattern area formed on a substrate which includes an inspection data generation means for generating inspection data in the inside and outside of a pattern area to be inspected, and a determination means for determining whether the pattern area is defective or not defective by comparing the inspection data of the inside of the pattern area generated by the inspection data generation means with predetermined inside reference inspection data and comparing the inspection data of the outside with predetermined outside reference inspection data is provided.

By the configuration, for example, because it is possible to apply a relaxed inspection reference to the inside part of the pad or wiring pattern to which a relatively large defect is allowed and a stricter inspection reference is applied to the outside part of the pad or wiring pattern to which even a fine defect is not allowed, it is possible to more precisely and effectively detect a defect of the substrate.

Further, in this invention, the type of the inspection data of the inside of the pattern area differs from the type of the inspection data of the outside of the pattern area.

In a preferred aspect, the inspection data of the inside of the pattern area is data about luminance and the inspection data of the outside of the pattern area is data about shapes.

By the configuration, with respect to the inside part, it is possible to accurately inspect whether a scratch exists or not based on the data about luminance. Also, with respect to the outside part, it is possible to accurately inspect whether a crack of the pad or a protrusion exists or not based on the data about positions.

Effects of the Invention

In the present invention, a substrate inspection apparatus for inspecting a formation state of a pattern area formed on a substrate which includes an inspection data generation means for generating inspection data in the inside and outside of a pattern area to be inspected, and a determination means for determining whether the pattern area is defective or not defective by comparing the inspection data of the inside of the pattern area generated by the inspection data generation means with predetermined inside reference inspection data and comparing the inspection data of the outside with predetermined outside reference inspection data is provided. By the configuration, for example, because it is possible to apply a relaxed inspection reference to the inside part of the pad or wiring pattern to which a relatively large defect is allowed and a stricter inspection reference is applied to the outside part of the pad or wiring pattern to which even a fine defect is not allowed, it is possible to more precisely and effectively detect a defect of the substrate.

BEST MODE FOR CARRYING OUT THE INVENTION

Figure 1:
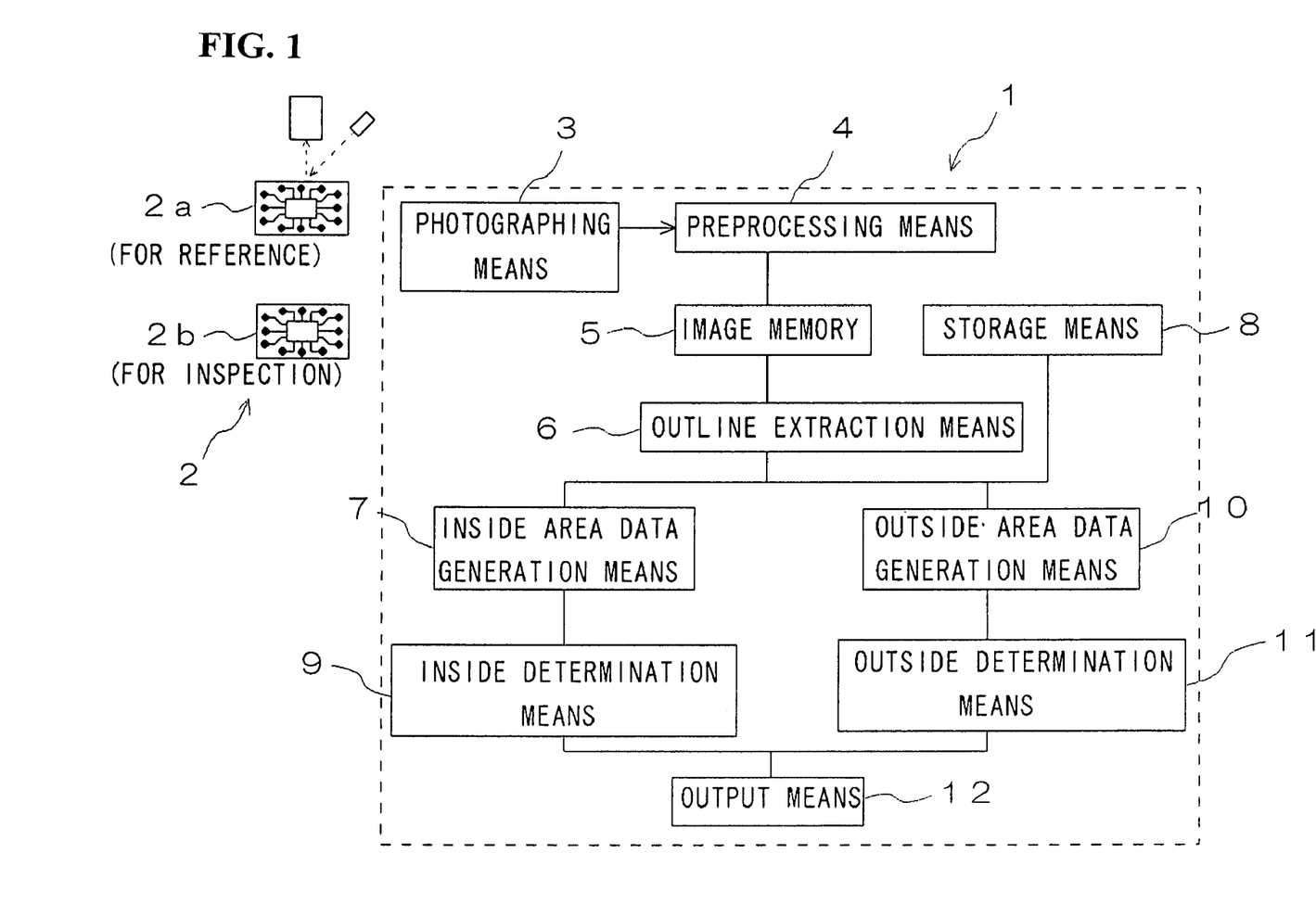
[FIG. 1] A block diagram of a substrate inspection apparatus according to an embodiment of the present invention.
Figure 2:
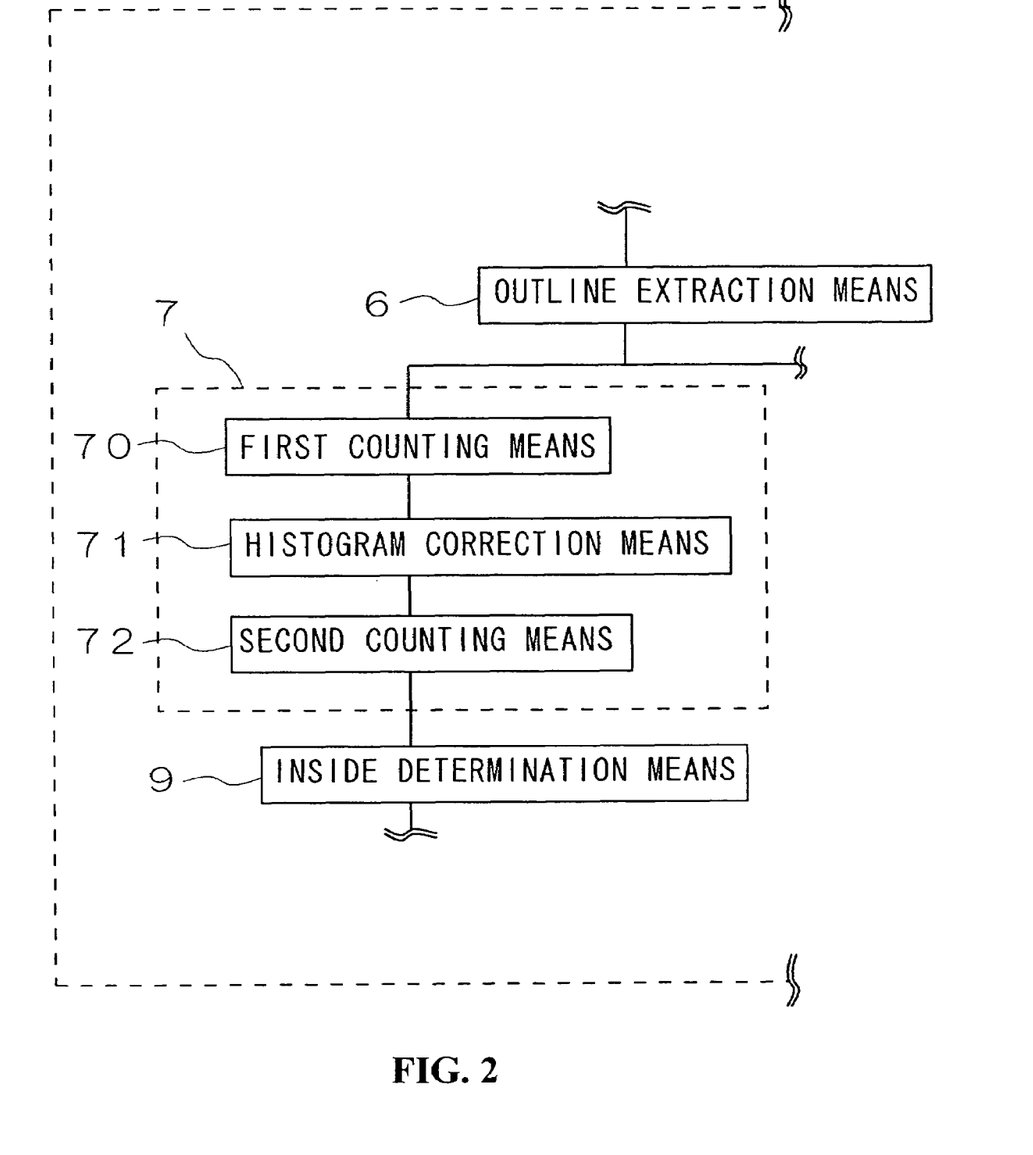
[FIG. 2] A detailed block diagram of an inside area data generation means according to the embodiment of the present invention.
Figure 3:
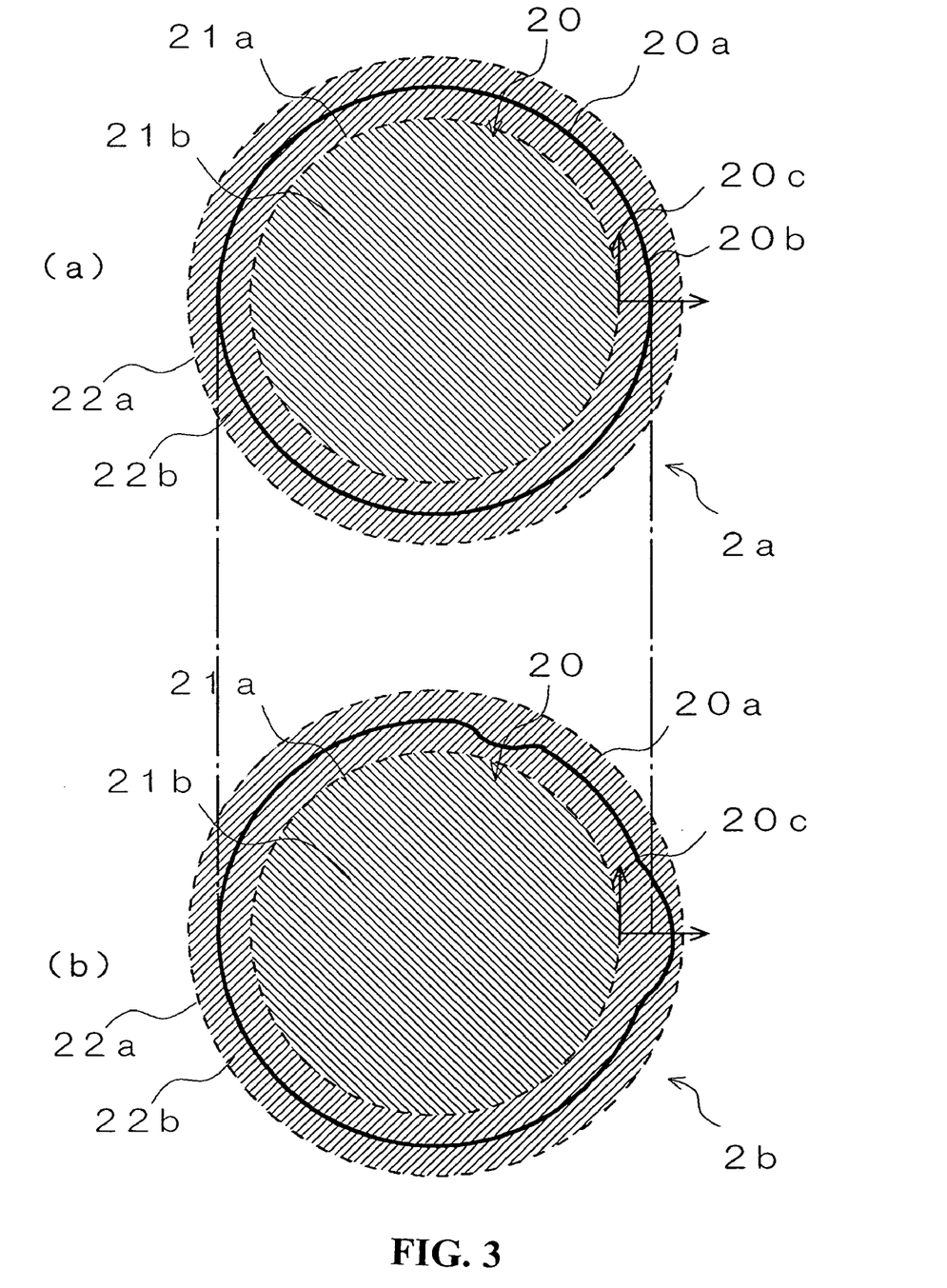
[FIG. 3] A view illustrating a relation between a pattern area formed and an inspection area according to the embodiment of the present invention.
Figure 4:
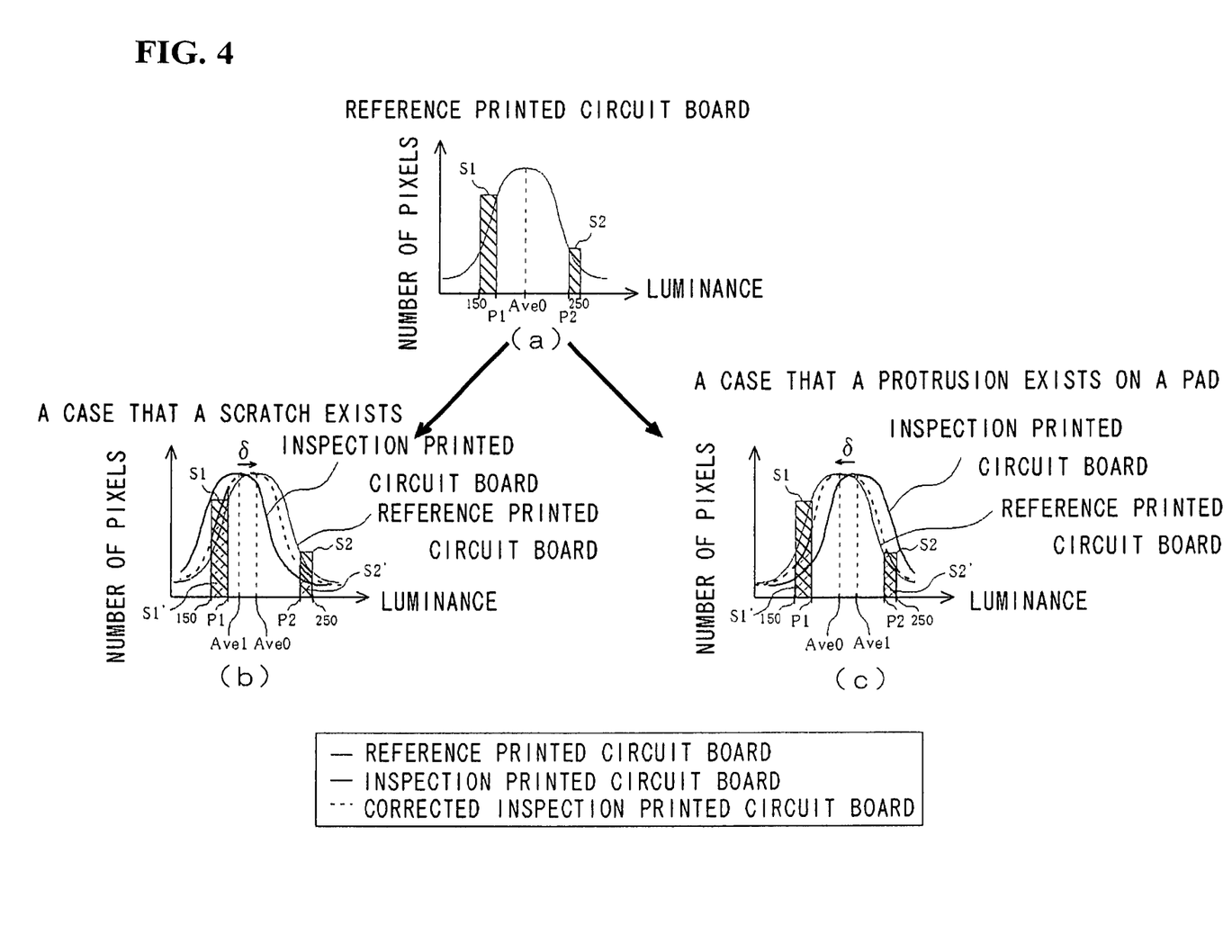
[FIG. 4] A view illustrating histograms of the inside area according to the embodiment of the present invention.
Figure 5:
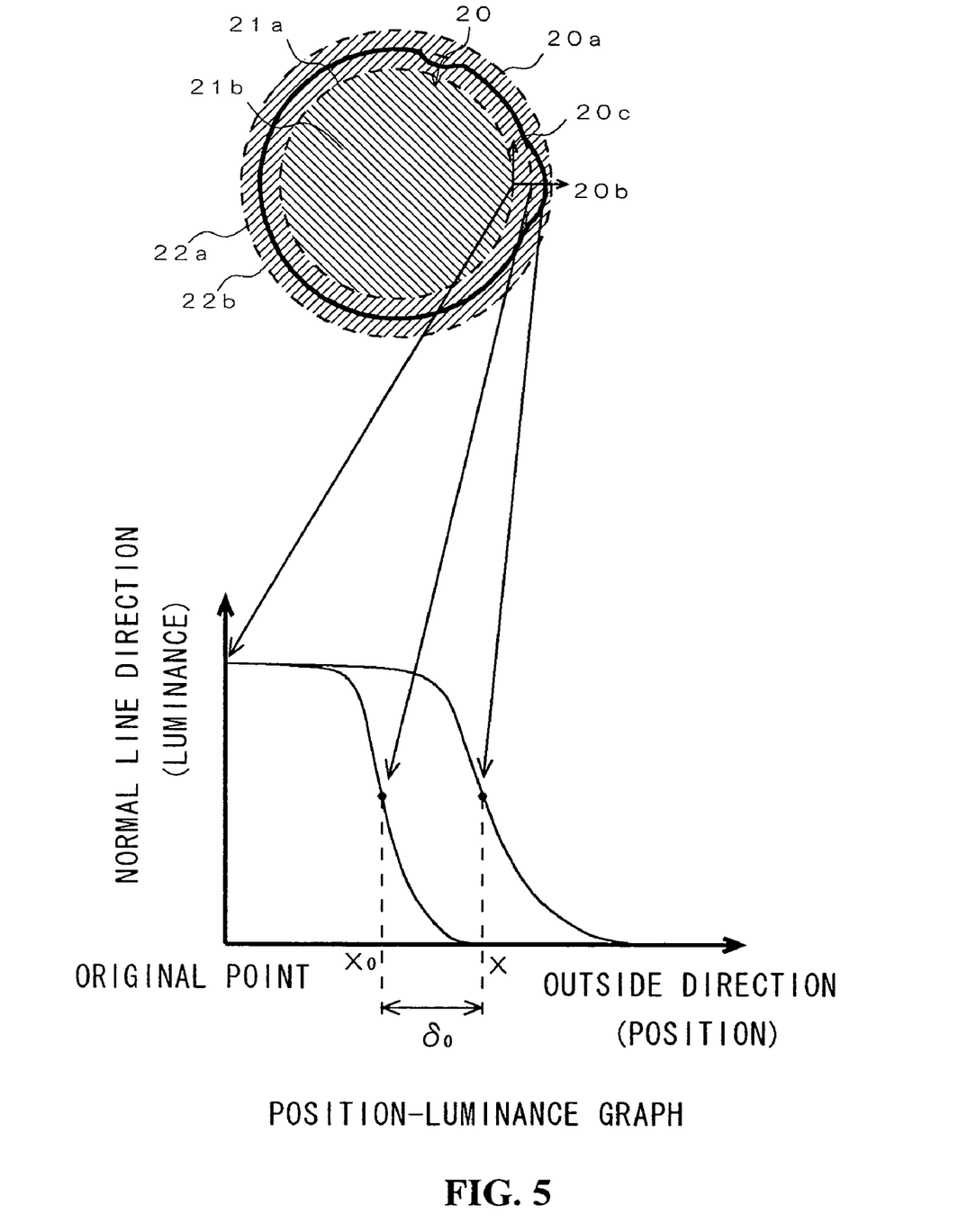
[FIG. 5] A view illustrating a position-luminance graph of an outside area according to the embodiment of the present invention.
Figure 6:
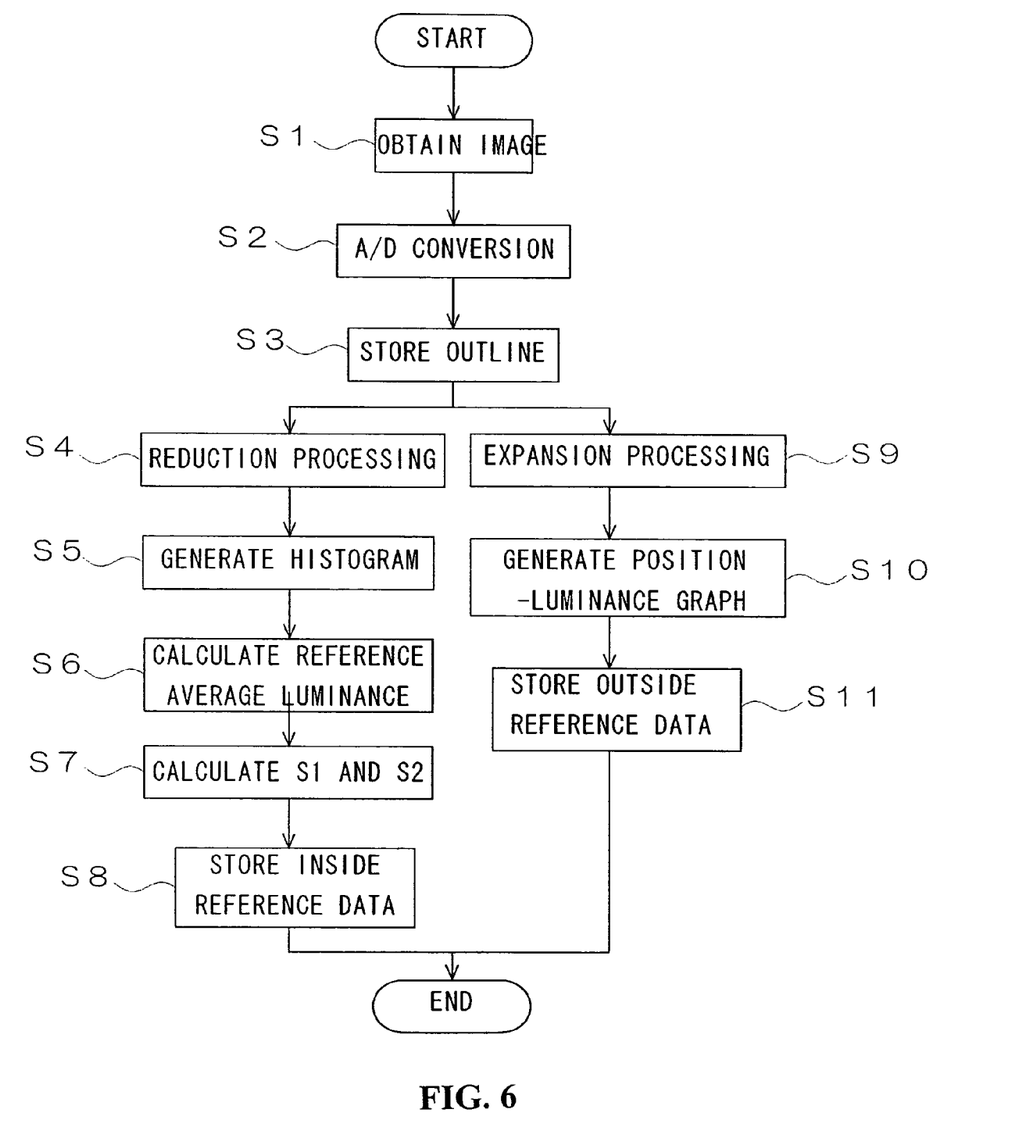
[FIG. 6] A flowchart for generating reference data according to the embodiment of the present invention.
Figure 7:
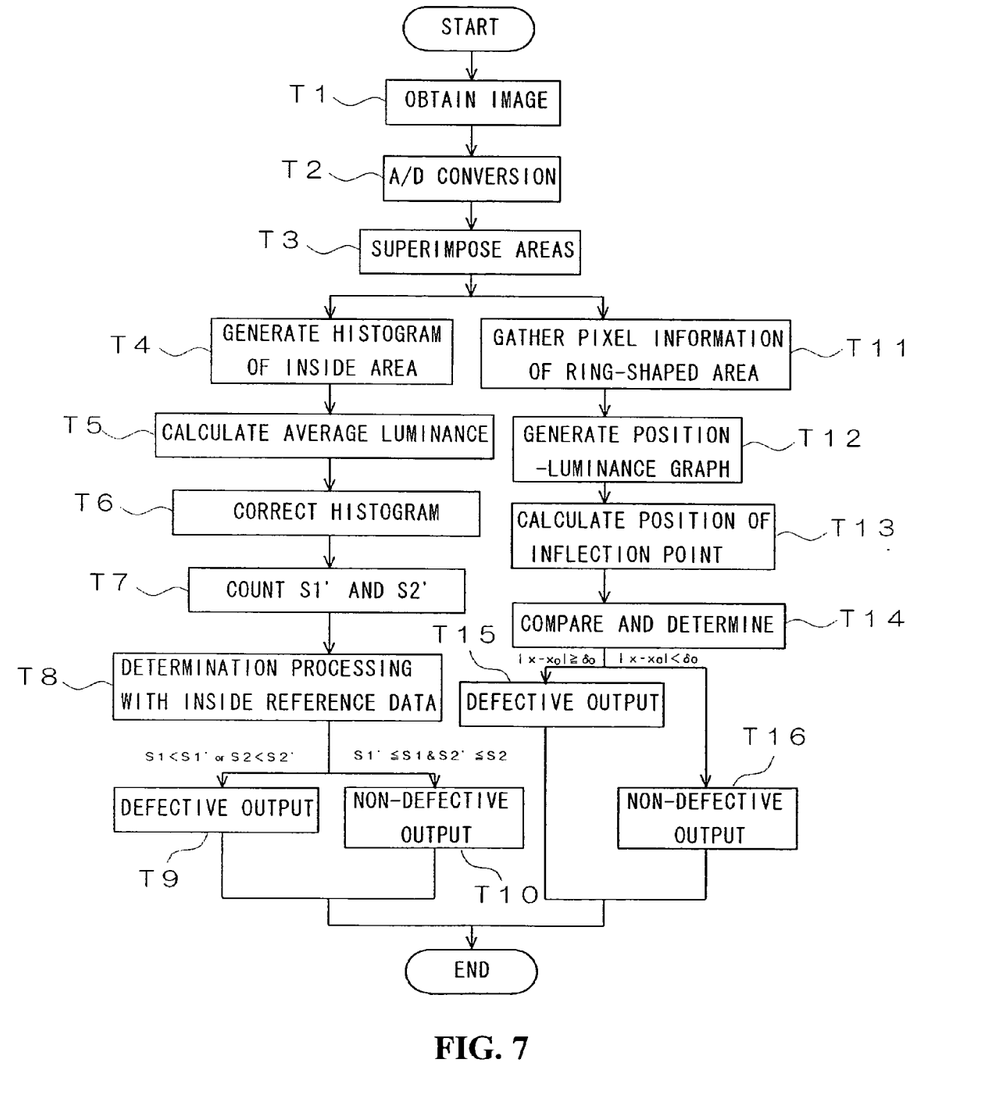
[FIG. 7] A flowchart when inspecting a printed circuit board according to the embodiment of the present invention.

Hereinafter, an embodiment of the present invention is described with reference to drawings. FIG. 1 illustrates a block diagram of a substrate inspection apparatus 1 according to the embodiment. FIG. 2 illustrates details of a block diagram of an inside area data generation means 7. FIG. 3 illustrates a relation between a pattern area formed on a printed circuit board 2 and an inspection area, and FIG. 3(a) illustrates a positional relation ship between a printed circuit board to be a reference (hereinafter, referred to as "reference printed circuit board ") 2a and the inside area and the outside area. FIG. 3(b) illustrates a relationship between a printed circuit board 2b to be inspected and the inside area and the outside area. FIG. 4 illustrates histograms which are used when determining a formation state of the inside area. FIG. 5 illustrates a position-luminance graph in an outside area to calculate a position of an outline part of a pattern area in the coordinate system. FIGS. 6 and 7 illustrate flowcharts which show operation of the substrate inspection apparatus 1.

In this embodiment, the substrate inspection apparatus 1 obtains an image in a pattern area 20 (see FIG. 3) on the printed circuit board 2 by using an photographing means 3 such as a camera and inspects the inside and the outside of the pattern area 20 by using different inspection references. In FIG. 3, a bold solid line and the inside of the bold solid line is the pattern area 20 formed on the printed circuit board 2. Hereinafter, a detailed description of a configuration of the substrate inspection apparatus 1 according to this embodiment is made.

In FIG. 1, the photographing means 3 captures a surface of the printed circuit board 2 to be inspected or a printed circuit board 2a which is to be a reference. In this embodiment, the photographing means 3 obtains the image of the surface by a gray scale of 256 gradations.

A preprocessing means 4 performs a processing such as an A/D conversion with respect to the image on the printed circuit board 2 captured by the CCD camera and temporarily stores the processed data on an image memory 5.

An outline extraction means 6 extracts an outline 20a of the pattern area 20 from the data processed by the preprocessing means 4, binarizes the obtained 256-gradation gray scale image by using a predetermined threshold, and data about the position of the binarized image is generated as the part changing from black to white or the part changing from white to black is the part of the outline 20a part.

An inside area data generation means 7 performs a reduction processing on the extracted outline 20a part to the inside and generates data about luminance within an inside area 21b (shaded part in a direction slanting to lower right) of an inside doted-line part in FIG. 3(a). Specifically, histograms about the inside area 21b to which the reduction processing is performed are generated and among the histograms, generates data for comparing with two reference values which are set to a light side and dark side in advance. In FIG. 2, a detailed block diagram of the inside area data generation means 7 is shown. The inside area data generation means 7 includes a first counting means 70 and a second counting means 72.

Between them, the first counting means 70 extracts and counts respectively, for example, pixels from luminance 150 to 250 out of images of the printed circuit board 2 stored on the image memory 5, and generates histograms of the reference printed circuit board 2a and histograms of the printed circuit board 2b to be inspected. FIGS. 4(a), (b), and (c) illustrate these histograms. In FIGS. 4(a), (b), and (c), a thin solid line shows the histogram of the reference printed circuit board 2a and a bold solid line shows the histogram of the printed circuit board 2b to be inspected. The histogram of the reference printed circuit board 2a is stored on a storage means 8, and with respect to the histogram of the printed circuit board 2b to be inspected, a correction processing is performed according to a color of the substrate, a color of the resist, whether a scratch on the surface of the pad exists or not etc. by a next histogram correction means 71.

The histogram correction means 71 calculates a reference average luminance Ave1 of the histogram of the printed circuit board 2b to be inspected while calculates a reference average luminance Ave0 of the histogram to the reference printed circuit board 2a, and corrects the number of pixels of each luminance of the printed circuit board 2b to be inspected so that the average luminance Ave1 corresponds to the Ave0. Describing the operation based on the histograms shown by the bold line in FIGS. 4(b) and (c), first, $\delta$=Ave0−Ave1 is calculated, the luminance of each pixel of the printed circuit board 2b to be inspected is shifted by $\delta$, and the histogram of the bold line is shifted to be the histogram shown by the bold dotted line. Then, based on the corrected histogram, data for indicating how much shifted to the light side, or inside reference data for indicating how much shifted to the dark side as compared with the histogram of the reference printed circuit board 2a is generated.

The second counting means 72, firstly, generates an inside reference data for indicating a permissible zone of shifts of a histogram. Specifically, as shown in FIG. 4(a), counts the number of pixels of a first luminance P1 which is set to a dark side in advance to the histogram of the reference printed circuit board 2a, while carrying out an operation of S1 (rectangular-shaped area part in FIG. 4) which is a value that the number of pixel is multiplied by a luminance width from a luminance 150 to the P1, counts the number of pixels to a second luminance P2, and carries out an operation of S2 (also, rectangular-shaped area part) which is a value that the number of pixel is multiplied by a luminance width from the luminance P2 to the 250. Then, the values are stored on the storage means 8 as the inside reference data. With respect to the printed circuit board 2b to be inspected, the corrected histogram is used, the number of pixels of each luminance which is darker than the first luminance P1 is counted and added respectively, and stored on the storage means 8 as S1'. Then, the number of pixels of each luminance which is lighter than the second luminance P2 is counted and added respectively as S2'. By using the S1', S1, and S2', S2, it is determined whether the formation state of the inside area 21b is good or bad.

An inside determination means 9 compares the number of pixels S1 and S2 which are the inside reference data of the reference printed circuit board 2a counted by the second counting means 72 with the number of pixels S1' and S2' which are the inside inspection data of the printed circuit board 2b to be inspected. If the number of pixels S1' is larger than S1, a decision that it is defective is output through an output means 12. If the number of pixels S2' is larger than S2, also, the decision that it is defective is output through the output means.

Next, a configuration of an outside area data generation means 10 is described. The outside area data generation means 10 generates data for determining a formation state of the outline 20a part of the pattern area 20, and generates outside area data to be reference (hereinafter, referred to as "outside reference data") and outside inspection data of the printed circuit board 2b to be inspected. With reference to FIG. 3, an outline of processing in the outside area data generation means 10 is described.

The outside area data generation means 10, first, in order to generate the outside reference data, while performs expansion processing to expand the outline 20a to the outside as shown by the outside dotted line part in FIG. 3(a), generates a spline 20b with respect to the outline 20a part extracted in the outline extraction means 6, and generates a graph with respect to luminance in an area (hereinafter, referred to as "ring-shaped area") 22b between the inside area 21b and the expansion-processed outline 22a in a normal line direction 20c of the spline 20b. FIG. 5 illustrates a graph about the position-luminance. In FIG. 5, an original point is set to the outline 20a part of the inside area 21b, and the direction of the outside area is set to the plus side. Generally, since the inside of the pattern area 20 is formed of a metal, the luminance is high. On the other hand, since the outside of the pattern area 20 is formed of a resist etc, the luminance is low. An inflection point of the graph is to be the outline 20a part of the pattern area 20. Then, the outside area data generation means 10 detects inflection points in all coordinate systems shifted by several pixels in the spline 20b direction, and stores the detected points on the storage means 8 as the outside reference data.

Next, the outside area data generation means 10 generates outside inspection data of the printed circuit board 2b to be inspected. Specifically, as shown in FIG. 3(b), the ring-shaped area 22b is superimposed on the pattern area 20 to be inspected, and as shown in FIG. 5, the graph about the luminance in the normal line direction 20c of the spline 20b is generated. Then, the inflection point x of the graph, that is, the position of the outline 20a in the coordinate system of the pattern area 20 to be inspected is detected, the position of the inflection point x in each coordinate system shifted by several pixels in the spline 20b direction is detected, and the outside inspection data is generated.

An outside determination means 11 compares thus generated outside reference data with the outside inspection data and determines whether a distance |x−x0| which is a distance of each inflection point x0 and x in each normal line direction 20c is within a predetermined reference value δ0 or not. In a case of |x−x0|>δ0, it is determined that a crack or protrusion exists in the outline 20a part and it is defective, and the determination is output through the output means 12. In a case of |x−x0|≦δ0, it is determined that a crack or protrusion does not exist in the outline 20a part and it is non-defective, and the determination is output through the output means 12.

With reference to FIGS. 6 and 7, a processing flow of thus configured substrate inspection apparatus 1 is described. First, in FIG. 6, a flow of generating reference data which is necessary when inspecting the printed circuit board 2b to be inspected is shown and in FIG. 7, a flow in a case of inspecting the printed circuit board 2b to be inspected is shown.

<Generation of Inside Reference Data and Generation Flow of Outside Reference Data>

First, when generating inside reference data, the reference printed circuit board 2a is attached on a predetermined position on the substrate inspection apparatus 1 by using a reference mark (not shown) which is formed on the surface and an image of the surface of the printed circuit board 2a is obtained by using the photographing means 3 (step S1). Then, the obtained image is converted by A/D conversion by the pre-processing means 4 (step S2), and the converted image information is written on the image memory 5. Thus obtained image is binarized by using a predetermined luminance value, and the part changing from black to white or the part changing from white to black is stored as the outline 20a part on the storage means 8 (step S3)

Then, a reduction processing is performed with respect to the outline 20a part (step S4), with respect to the reduced inside area 21b, each of the number of pixels of luminance from luminance 150 to 250 out of the gray scale of 256 gradations is counted, and a histogram as shown in FIG. 4(a) is generated (step S5). Then, first, from the generated histogram, a reference average luminance Ave0 is obtained (step S6). To the predetermined first luminance P1 and the predetermined second luminance P2, the number of pixels of the first luminance P1 and the second luminance P2 are counted, the number of pixels S1 which is obtained by multiplying the number of pixels of the first luminance P1 by a luminance width from the luminance 150 to P1, and the number of pixels S2 which is obtained by multiplying the number of pixels of the second luminance P2 by a luminance width from the luminance P2 to 250 are calculated (step S7), and the number of pixels S1 and the number of pixels S2 are stored as the inside reference data on the storage means 8 (step S8).

When outside reference data is generated, first, expansion processing is performed with respect to the outline 20a part (step S9), and information about pixels from the reduced area to the outside ring-shaped area 22b is gathered. Then, as shown in FIG. 5, a position-luminance graph with respect to the normal line direction 20c of the spline 20b of the outline 20a is generated (step S10), in the graph, the position x0 of an inflection point where the differential value of luminance makes the largest change is calculated. Then, information about an inflection point in each coordinate system in which the inflection point is shifted by several pixels in the spline 20b direction is stored as the outside reference data on the storage means 8 (step S11).

Then, the reference printed circuit board 2a is detached from the substrate inspection apparatus 1, and prepared for an inspection of the printed circuit board 2b to be inspected.

<Inspection Processing of Printed Circuit Board 2 to be Inspected>

When a formation state of the printed circuit board 2b to be inspected is inspected, similarly, first, attached to a predetermined position on the substrate inspection apparatus 1 by using the reference mark, and an image of the surface of the printed circuit board 2b is obtained (step T1). Then, the obtained image is converted by A/D conversion by the pre-processing means 4 (step T2), and the information is written on the image memory 5.

Then, the positional information of the inside area 21b of the reference printed circuit board 2a which has already stored on the storage means 8 is read, superimposed on the pattern area 20 of the printed circuit board 2b to be inspected (step T3), and information about the inside pixels is gathered. Similarly, with respect to the area, the number of pixels of luminance from luminance 150 to 250 by the gray scale of 256 gradations is counted, while histograms shown in FIGS. 4(b) and (c) by the bold solid line are generated (step T4), an average luminance Ave1 is calculated from the generated histograms (step T5). Then, a difference δ between the calculated average luminance Ave1 and the reference average luminance Ave0 of the reference printed circuit board 2a is calculated, and a correction processing in which each luminance in the histogram generated in step T3 is shifted by the amount of δ is performed (step T6). Based on the corrected histogram, while each of the number of pixels S1' which has darker luminance than the predetermined first luminance P1 is calculated, each of the number of pixels S2' which has lighter luminance than the second luminance P2 is calculated (step T7), according to a determination with the inside reference data S1 and S2 (step T8), an output of a determination that the printed circuit board 2b is defective is performed (step T9). Further, also, when the number of pixels S2' of the printed circuit board 2b to be inspected is larger than the number of pixels S2 of the reference printed circuit board 2a (step T7), an output of a determination that the printed circuit board 2b is defective is performed (step T9). That is, when S1' is larger than the first reference number of pixels S1, because the possibility that a crack exists more than a scratch by polishing is high, it is determined to be defective. Also, when S2' is larger than the second reference number of pixels S2, because the possibility that a protrusion etc. exists on a pad is high, it is determined to be defective. On the other hand, if S1'≦S1 and S2'≦S2 (step T8), it is determined that the printed circuit board 2b is non-defective and the determination is output (step T10).

Then, in order to inspect a formation state of the outline 20a part, information about pixels in the ring-shaped area 22b where the ring-shaped area 22b of the reference printed circuit board 2a is superimposed on the pattern area 20 to be inspected is gathered (step T11). With respect to the ring-shaped area 22b, a position-luminance graph about luminance in the normal line direction 20c of the spline 20b of the reference printed circuit board 2a is generated (step T12), and an inflection point in the graph is detected (step T13). A similar processing is performed by shifting by several pixels in the spline 20b direction, a distance δ0 between a position x of the detected inflection point and a position x0 of the inflection point which has already been stored on the storage means 8 is compared and determined (step T14), if the distance exceeds a predetermined threshold δ0, an output of a determination that it is defective is performed (step T15). On the other hand, if the distance between the position x of the detected inflection point and the position x0 of the inflection point which has already been stored on the storage means 8 is within the predetermined threshold δ0, an output of a determination that it is non-defective is performed (step T16).

As described above, according to this embodiment, in the substrate inspection apparatus 1 for inspecting a formation state of the pattern area 20 such as a pad or wiring pattern formed on the printed circuit board 2b, since the inside area data generation means 7 for generating inspection data of the inside area 21b of the pattern area 20 to be inspected, the outside area data generation means 10 for generating inspection data of the ring-shaped area 22b of the outside, and the inside determination means 9 and the outside determination means 11 for determining whether the pattern area 20 is defective or not defective by comparing the generated inside area data with the predetermined inside reference data and comparing the outside area data with the outside reference data are provided, by applying a relaxed inspection reference to the inside area 21b of the pattern area 20 where a relatively large defect is allowed and applying a strict inspection reference to the ring-shaped area 22b of the pattern area 20 where even a fine defect is not allowed, it is possible to precisely and effectively detect a defect of the printed circuit board 2b.

Further, in this embodiment, since the type of the inside area data is data about luminance, that is, data which indicates shifts of histograms, it is possible to accurately inspect a scratch or unevenness in the inside area 21b, and since the type of the outside area data is data about positions of the outline 20a, it is possible to accurately inspect a crack or a protruding part in the outline 20a part.

The present invention is not limited to the above embodiment, can be applied in various modifications.

For example, in the above embodiment, the inspection of the printed circuit board 2 is exemplarily described, however, it is not limited to the above, applicable to a case of inspecting a pattern on a glass substrate.

Further, in the above embodiment, the data which indicates shifts of the histograms is to be the inside area data and the data which indicates the position of the outline 20a of the pattern area 20 is to be the outside area data. However, it is not limited to the above, any method can be applied if the method inspects the inside area and the outside area by using different reference values.

INDUSTRIAL APPLICABILITY

When inspecting a formation state of the pattern area 20 formed on the printed circuit board 1, by independently inspecting the inside area 21c of the pattern area 20 and the ring-shaped area 22b of the outside respectively, it is possible to apply a relaxed reference to the inside of the pattern area 20 where a relatively large defect is allowed and apply a strict reference to the outside of the pattern area 20 where even a fine defect is not allowed. Further, particularly, with respect to the ring-shaped area 22b, since a determination reference about shapes is used to inspect, it is possible to prevent a short circuit etc. with the adjacent pattern area 20.

DESCRIPTION OF REFERENCE NUMERALS

1 . . . Substrate inspection apparatus
2a, 2b . . . Printed circuit board (2a: Reference printed circuit board, 2b: Printed circuit board to be inspected)
7 . . . Inside area data generation means
9 . . . Inside determination means
10 . . . Outside area data generation means
11 . . . Outside determination means
20 . . . Pattern area
21a . . . Outline of inside area
21b . . . Inside area
22a . . . Outline of outside area
22b . . . Ring-shaped area

The invention claimed is:

1. A substrate inspection apparatus for inspecting a formation state of a pattern area formed on a substrate, the substrate inspection apparatus comprising:

an inside area data generation means for generating a first inspection data of an inside area of a pattern area to be inspected, the inside area data generation means performing a reduction processing of the inside area to generate the first inspection data, an outside area data generation means for generating a second inspection data of an outside area of the pattern area, the outside area surrounding the inside area, the outside area data generation means performing an expansion processing of the outside area to generate the second inspection data;

an inside determination means for determining whether the pattern area is defective or not defective by comparing the first inspection data with predetermined inside reference inspection data; and an outside determination means for determining whether the pattern area is defective by comparing the second inspection data with predetermined outside reference inspection data.

2. The substrate inspection apparatus according to claim 1, wherein the first inspection data differs form the second inspection data.

3. The substrate inspection apparatus according to claim 1, wherein the first inspection data is data about luminance and the second inspection data is data about shapes.

4. The substrate inspection apparatus according to claim 1, wherein a stricter inspection reference is applied to the outside area than to the inside area.

5. The substrate inspection apparatus according to claim 1, wherein the outside area data generation means generates the second inspection data based on luminance in a normal direction of the pattern area.

6. The substrate inspection apparatus according to claim 1, wherein the outside area data generation means detects inflection points in a position-luminance graph as the second inspection data, and wherein the outside determination means determines whether the pattern area is defective by comparing the second inspection data with predetermined outside reference inspection data.

* * * * *